(12) United States Patent
Jaffe et al.

(10) Patent No.: US 6,837,846 B2
(45) Date of Patent: Jan. 4, 2005

(54) ENDOSCOPE HAVING A GUIDE TUBE

(75) Inventors: Ross Jaffe, Atherton, CA (US); Joseph M. Tartaglia, Morgan Hill, CA (US); Amir Belson, Cupertino, CA (US)

(73) Assignee: Neo Guide Systems, Inc., Los Gatos, CA (US)

( * ) Notice: Subject to any disclaimer, the term of this patent is extended or adjusted under 35 U.S.C. 154(b) by 0 days.

(21) Appl. No.: 10/139,289

(22) Filed: May 2, 2002

(65) Prior Publication Data

US 2002/0161281 A1 Oct. 31, 2002

Related U.S. Application Data

(63) Continuation-in-part of application No. 09/969,927, filed on Oct. 2, 2001, now Pat. No. 6,610,007, which is a continuation-in-part of application No. 09/790,204, filed on Feb. 20, 2001, now Pat. No. 6,468,203.
(60) Provisional application No. 60/194,140, filed on Apr. 3, 2000.

(51) Int. Cl.[7] .................................................. A16B 1/00
(52) U.S. Cl. .................................................... 600/114
(58) Field of Search ................................ 600/114, 121, 600/124, 139, 144, 146

(56) References Cited

U.S. PATENT DOCUMENTS

| | | |
|---|---|---|
| 2,767,705 A | 10/1956 | Moore |
| 3,060,972 A | 10/1962 | Sheldon |
| 3,610,231 A | 10/1971 | Takahashi et al. |
| 3,739,770 A | 6/1973 | Mori |
| 3,773,034 A | 11/1973 | Burns et al. |
| 3,897,775 A | 8/1975 | Furihata |
| 3,946,727 A | 3/1976 | Okada et al. |
| 4,054,128 A | 10/1977 | Seufert et al. |
| 4,176,662 A | 12/1979 | Frazer |
| 4,236,509 A | 12/1980 | Takahashi et al. |
| 4,273,111 A | 6/1981 | Tsukaya |
| 4,327,711 A | 5/1982 | Takagi |
| 4,432,349 A | 2/1984 | Oshiro |
| 4,499,895 A | 2/1985 | Takayama |
| 4,503,842 A | 3/1985 | Takayama |
| 4,543,090 A | 9/1985 | McCoy |

(List continued on next page.)

FOREIGN PATENT DOCUMENTS

| | | |
|---|---|---|
| DE | 37 07 787 | 9/1988 |
| JP | 63 136014 | 6/1988 |
| JP | 111458 A | 5/1993 |
| JP | 5-1999 A | 10/1993 |
| WO | WO 01/74235 | 10/2001 |
| WO | WO 03/028547 | 4/2003 |

OTHER PUBLICATIONS

Hasson, H.M., M.D., (May 1979) Technique of open laparoscopy: Equipment and Technique (from step 1 to step 9), 2424 North Clark Street, Chicago, Illinois 60614, 3 pages.

(List continued on next page.)

*Primary Examiner*—Beverly M. Flanagan
(74) *Attorney, Agent, or Firm*—Wilson Sonsini Goodrich & Rosati (57) ABSTRACT

An endoscope having a guide tube is described herein. The assembly has an endoscope which is slidably insertable within the lumen of a guide tube. The guide tube is configured to be rigidizable along its entire length from a relaxed configuration. The endoscope has a steerable distal portion to facilitate the steering of the device through tortuous paths. In the relaxed configuration, a portion of the guide tube is able to assume the shape or curve defined by the controllable distal portion of the endoscope. Having assumed the shape or curve of the endoscope, the guide tube may be rigidized by the physician or surgeon to maintain that shape or curve while the endoscope is advanced distally through the tortuous path without having to place any undue pressure against the tissue walls.

28 Claims, 9 Drawing Sheets

U.S. PATENT DOCUMENTS

| | | | |
|---|---|---|---|
| 4,559,928 A | 12/1985 | Takayama | |
| 4,592,341 A | 6/1986 | Omagari et al. | |
| 4,621,618 A | 11/1986 | Omagari | |
| 4,630,649 A | 12/1986 | Oku | |
| 4,646,722 A | 3/1987 | Silverstein et al. | |
| 4,651,718 A | 3/1987 | Collins et al. | |
| 4,686,963 A | 8/1987 | Cohen et al. | |
| 4,753,223 A | 6/1988 | Bremer | |
| 4,788,967 A | 12/1988 | Ueda | |
| 4,793,326 A | 12/1988 | Shishido | |
| 4,796,607 A | 1/1989 | Allred, III et al. | |
| 4,799,474 A | 1/1989 | Ueda | |
| 4,815,450 A | 3/1989 | Patel | |
| 4,832,473 A | 5/1989 | Ueda | |
| 4,834,068 A | 5/1989 | Gottesman | |
| 4,873,965 A | 10/1989 | Danieli | |
| 4,879,991 A | 11/1989 | Ogiu | |
| 4,884,557 A | 12/1989 | Takehana et al. | |
| 4,890,602 A | 1/1990 | Hake | |
| 4,895,431 A | 1/1990 | Tsujiuchi et al. | |
| 4,899,731 A | 2/1990 | Takayama et al. | |
| 4,904,048 A | 2/1990 | Sogawa et al. | |
| 4,930,494 A * | 6/1990 | Takehana et al. | 600/145 |
| 4,957,486 A | 9/1990 | Davis | |
| 4,969,709 A | 11/1990 | Sogawa et al. | |
| 4,971,035 A | 11/1990 | Ito | |
| 4,977,887 A * | 12/1990 | Gouda | 600/144 |
| 4,987,314 A | 1/1991 | Gotanda et al. | |
| 5,018,509 A | 5/1991 | Suzuki et al. | |
| 5,125,395 A | 6/1992 | Adair | |
| 5,127,393 A | 7/1992 | McFarlin et al. | |
| 5,159,446 A | 10/1992 | Hibino et al. | |
| 5,243,967 A | 9/1993 | Hibino | |
| 5,251,611 A * | 10/1993 | Zehel et al. | 600/141 |
| 5,271,381 A | 12/1993 | Ailinger et al. | |
| 5,337,732 A | 8/1994 | Grundfest et al. | |
| 5,337,733 A * | 8/1994 | Bauerfeind et al. | 600/139 |
| 5,370,108 A | 12/1994 | Miura et al. | |
| 5,383,852 A | 1/1995 | Stevens-Wright | |
| 5,394,864 A | 3/1995 | Kobayashi et al. | |
| 5,400,769 A | 3/1995 | Tanii et al. | |
| 5,429,118 A * | 7/1995 | Cole et al. | 600/121 |
| 5,460,166 A | 10/1995 | Yabe et al. | |
| 5,460,168 A | 10/1995 | Masubuchi et al. | |
| 5,469,840 A | 11/1995 | Tanii et al. | |
| 5,482,029 A | 1/1996 | Sekiguchi et al. | |
| 5,487,757 A | 1/1996 | Truckai et al. | |
| 5,507,717 A | 4/1996 | Kura et al. | |
| 5,531,664 A | 7/1996 | Adachi et al. | |
| 5,551,945 A | 9/1996 | Yabe et al. | |
| 5,558,619 A | 9/1996 | Kami et al. | |
| 5,577,992 A | 11/1996 | Chiba et al. | |
| 5,624,380 A | 4/1997 | Takayama et al. | |
| 5,624,381 A | 4/1997 | Kieturakis | |
| 5,626,553 A | 5/1997 | Frassica et al. | |
| 5,645,520 A | 7/1997 | Nakamura et al. | |
| 5,658,238 A | 8/1997 | Suzuki et al. | |
| 5,662,587 A | 9/1997 | Grundfest et al. | |
| 5,665,050 A | 9/1997 | Benecke | |
| 5,667,476 A | 9/1997 | Frassica et al. | |
| 5,733,245 A | 3/1998 | Kawano | |
| 5,749,828 A | 5/1998 | Solomon et al. | |
| 5,752,912 A | 5/1998 | Takahashi et al. | |
| 5,759,151 A * | 6/1998 | Sturges | 600/146 |
| 5,779,624 A | 7/1998 | Chang | |
| 5,810,715 A | 9/1998 | Moriyama | |
| 5,860,914 A | 1/1999 | Chiba et al. | |
| 5,876,373 A | 3/1999 | Giba et al. | |
| 5,885,208 A | 3/1999 | Moriyama | |
| 5,897,488 A | 4/1999 | Ueda | |
| 5,906,591 A | 5/1999 | Dario et al. | |
| 5,916,147 A | 6/1999 | Boury | |
| 5,921,915 A | 7/1999 | Aznoian et al. | |
| 5,941,815 A | 8/1999 | Chang | |
| 5,976,074 A | 11/1999 | Moriyama | |
| 5,989,182 A | 11/1999 | Hori et al. | |
| 5,989,230 A | 11/1999 | Frassica | |
| 5,993,381 A | 11/1999 | Ito | |
| 6,036,636 A | 3/2000 | Motoki et al. | |
| 6,066,132 A | 5/2000 | Chen et al. | |
| 6,099,485 A | 8/2000 | Patterson | |
| 6,149,581 A | 11/2000 | Klingenstein | |
| 6,162,171 A | 12/2000 | Ng et al. | |
| 6,174,280 B1 * | 1/2001 | Oneda et al. | 600/121 |
| 6,179,776 B1 | 1/2001 | Adams et al. | |
| 6,210,337 B1 | 4/2001 | Dunham et al. | |
| 6,221,006 B1 | 4/2001 | Dubrul et al. | |
| 6,270,453 B1 | 8/2001 | Sakai | |
| 6,309,346 B1 | 10/2001 | Farhadi | |
| 6,402,687 B1 | 6/2002 | Ouchi | |
| 6,408,889 B1 | 6/2002 | Komachi | |
| 6,468,203 B2 | 10/2002 | Belson | |
| 6,482,149 B1 | 11/2002 | Torii | |
| 6,610,007 B2 | 8/2003 | Belson et al. | |
| 2002/0120178 A1 | 8/2002 | Tartaglia et al. | |
| 2003/0083550 A1 | 5/2003 | Miyagi | |

OTHER PUBLICATIONS

McKernan "History: laparoscopie general surgery: from 1983 to Apr. 11, 1989" 4 pages.

Lee, T.S. et al., (1994). "A Highly Redundant Robot System For Inspection," Proceedings of Conference on Intelligent Robots in Factory, Fields, Space and Service. Houston, TX Mar. 21–24 1994 Part vol. 1:142–148.

Slatkin et al. (Aug. 1995). "The Development of a Robotic Endoscope," Proceedings 1995. IEEE/RSJ International Conference on Human Robot Interaction and Cooperative Robots. Pittsburgh, PA Aug. 5–9, 1995, Proceeding of the IEEE/RSJ International Conference on Intelligent Robot Syst. 2:162–171.

* cited by examiner

ENDOSCOPE HAVING A GUIDE TUBE

CROSS-REFERENCE TO RELATED APPLICATIONS

This is a continuation-in-part of U.S. patent application Ser. No. 09/969,927 filed Oct. 2, 2001, now U.S. Pat. No. 6,610,007 which is a continuation-in-part of U.S. patent application Ser. No. 09/790,204 filed Feb. 20, 2001, now U.S. Pat. No. 6,468,203 which claims priority of U.S. Provisional Patent Application Ser. No. 60/194,140 filed Apr. 3, 2000, each of which is incorporated herein by reference in its entirety.

FIELD OF THE INVENTION

The present invention relates generally to endoscopes and endoscopic medical procedures. More particularly, it relates to a method and apparatus to facilitate insertion of a flexible endoscope along a tortuous path using a guide tube apparatus, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135–185 cm in length and 12–19 mm in diameter, and includes a fiberoptic imaging bundle or a miniature camera located at the instrument's tip, illumination fibers, one or two instrument channels that may also be used for insufflation or irrigation, air and water channels, and vacuum channels.

The colonoscope is inserted via the patient's anus and is advanced through the colon, allowing direct visual examination of the colon, the ileocecal valve and portions of the terminal ileum. Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation.

Steerable colonoscopes have been devised to facilitate selection of the correct path though the curves of the colon. However, as the colonoscope is inserted farther and farther into the colon, it becomes more difficult to advance the colonoscope along the selected path. At each turn, the wall of the colon must maintain the curve in the colonoscope. The colonoscope rubs against the mucosal surface of the colon along the outside of each turn. Friction and slack in the colonoscope build up at each turn, making it more and more difficult to advance and withdraw the colonoscope. In addition, the force against the wall of the colon increases with the buildup of friction. In cases of extreme tortuosity, it may become impossible to advance the colonoscope all of the way through the colon.

Steerable endoscopes, catheters and insertion devices for medical examination or treatment of internal body structures are described in the following U.S. patents, the disclosures of which are hereby incorporated by reference in their entirety: U.S. Pat. Nos. 4,543,090; 4,753,223; 5,337,732; 5,337,733; 5,383,852; 5,487,757 and 5,662,587.

BRIEF SUMMARY OF THE INVENTION

An endoscopic assembly and method of advancing the assembly which is able to traverse tortuous paths, such as the colon, without excessively contacting the walls of the colon is described herein. The assembly generally comprises a combination of an endoscope which is slidably insertable within the lumen of a guide tube. The endoscope may be any conventional endoscope having a shaft which extends from a handle. The distal end of the shaft preferably comprises a controllable distal portion which may be manipulated to facilitate the steering of the assembly through the tortuous path. The guide tube may be a conventional flexible conduit which is configured to be rigidizable along its entire length from a relaxed configuration. In the relaxed configuration, a portion of the guide tube is able to assume the shape or curve defined by the controllable distal portion of the endoscope. Having assumed the shape or curve of the endoscope, the guide tube may be rigidized by the physician or surgeon to maintain that shape or curve.

Alternatively, the guide tube may also be used with an endoscope having an automatically controlled proximal portion and a selectively steerable distal portion. Such a controllable endoscope may have a distal portion which is manually steerable by the physician or surgeon to assume a shape to traverse an arbitrary curved path and a proximal portion which is automatically controlled by, e.g., a computer, to transmit the assumed shape along the proximal portion as the endoscope is advanced or withdrawn. More detailed examples are described in copending U.S. patent application Ser. No. 09/969,927, which has been incorporated above by reference in its entirety.

The guide tube may be comprised of a plurality of individual segments which are linked adjacent to one another via one or more tensioning wires or elements. These tensioning elements may be placed circumferentially about each of the segments and preferably run throughout the length of the guide tube through each of the individual segments. When the guide tube is to be rigidized, the tensioning elements may be pulled or tightened to draw the segments together such that the entire guide tube becomes rigid. The tensioning elements may then be loosened such that the individual segments may move relative to one another.

In use, e.g., in the colon, the physician or surgeon may typically first advance the distal portion of the endoscope within the body of the patient. When the first curve of the colon is approached, the user may appropriately steer the distal portion of the endoscope to assume a curve for traversing the path. At this point, the endoscope is preferably held stationary relative to the patient while the guide, in a relaxed and flexible state, is advanced over the shaft of the endoscope until the distal end of the guide tube is at, or a short distance past, the distal tip of the endoscope. Once the guide tube, or at least its distal portion, has assumed the curve formed by the controllable distal portion of the endoscope, the guide tube may then be rigidized, preferably along its length, to hold its assumed shape. Once this is done, the endoscope may be further advanced within the rigidized guide tube to traverse the curved pathway without having to place any pressure against the walls of the colon. The steps for advancing the endoscope may be repeated as necessary until the desired area within the body has been reached.

At any point during the exploratory procedure, the guide tube may be removed from the colon while leaving the endoscope behind. To remove the assembly from the colon, the guide tube may first be withdrawn and the endoscope may be subsequently withdrawn. Alternatively, the above steps may be repeated in reverse order to withdraw both the guide tube and the endoscope from the region.

The outer surface of the guide tube preferably has a tubular covering which covers at least a majority of the tube to prevent the entry of debris and fluids within the lumen of the guide tube between the individual segments. The covering also facilitates the advancement and withdrawal of the guide tube by preventing tissue from being pinched between the segments. To prevent tissue from being pinched between the guide tube and endoscope during assembly movement, expandable bellows or an additional covering may optionally be placed over the distal opening of the guide tube. This additional covering may simply be an integral extension of the covering over the surface of the guide tube, or it may be a separate covering attached to the distal end of the guide tube. This covering may also be attached to or near the distal end of the endoscope to maintain a seal between the endoscope shaft and the guide tube. The coverings and their variations may be attached by any conventional method as practicable. If the covering over the distal end of the guide tube is utilized, as the distal portion of the endoscope shaft is advanced distally through the guide tube, the covering preferably expands distally along with the endoscope or simply slides distally along with the endoscope. When the shaft is retracted within the guide lumen, the covering again preferably retracts proximally along with the proximal movement of the distal end of the endoscope or it may simply be retracted manually along with the endoscope. The use of the additional covering may also aid in maintaining the sterility of the internal lumen of the guide tube.

DETAILED DESCRIPTION OF THE INVENTION

Figure 1:
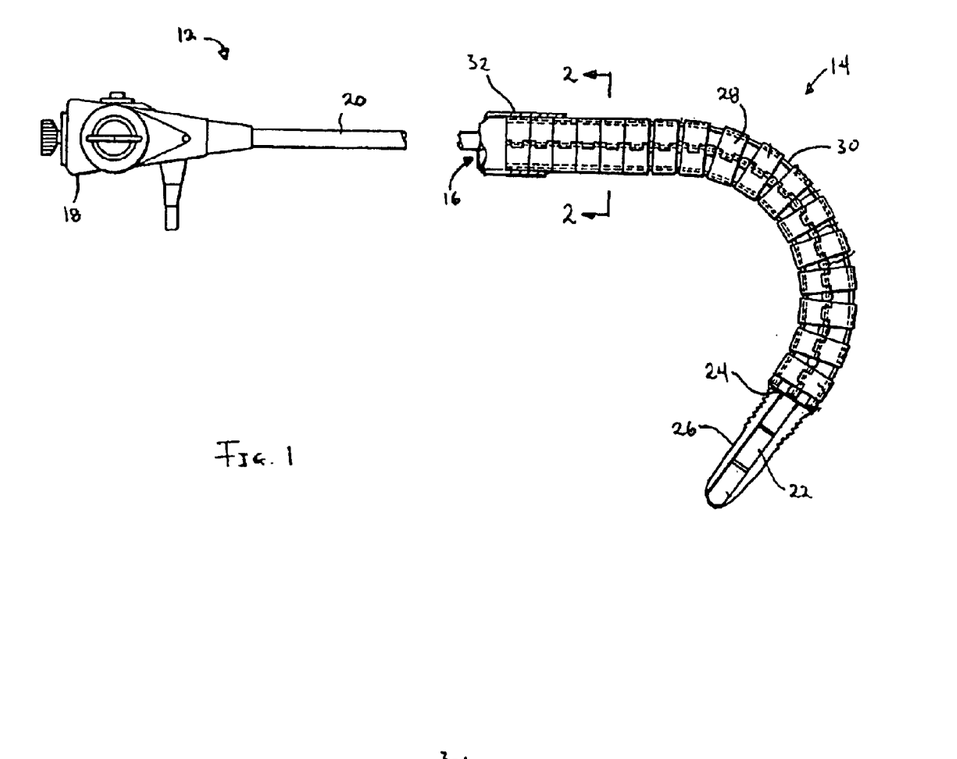
FIG. 1 shows a variation of the guide tube assembly in which an endoscope is pushed through and supported by a guide tube.

As shown in FIG. 1, a representative illustration of a variation on guide tube assembly 10 is seen partially disassembled for clarity. Assembly 10 generally comprises an endoscope 12 which is insertable within guide tube 14 through guide lumen 16. Endoscope 12 may be any conventional type endoscope having a handle 18 with shaft 20 extending therefrom. The distal end of shaft 20 preferably comprises a controllable distal portion 22 which may be manipulated to facilitate the steering of the device through the body. Endoscope shaft 20 may be slidingly disposed within guide lumen 16 such that controllable distal portion 22 is able to be passed entirely through guide tube 14 and out distal opening 24 defined at the distal end of tube 14.

Alternatively, guide tube 14 may also be used with an endoscope having an automatically controlled proximal portion and a selectively steerable distal portion, as described in further detail below. Such a controllable endoscope may have a distal portion which is manually steerable by the physician or surgeon to assume a shape to traverse an arbitrary curved path and a proximal portion which is automatically controlled by, e.g., a computer, to transmit the assumed shape along the proximal portion as the endoscope is advanced or withdrawn. More detailed examples are described in copending U.S. patent application Ser. No. 09/969,927, which has been incorporated above by reference in its entirety.

Figure 4:
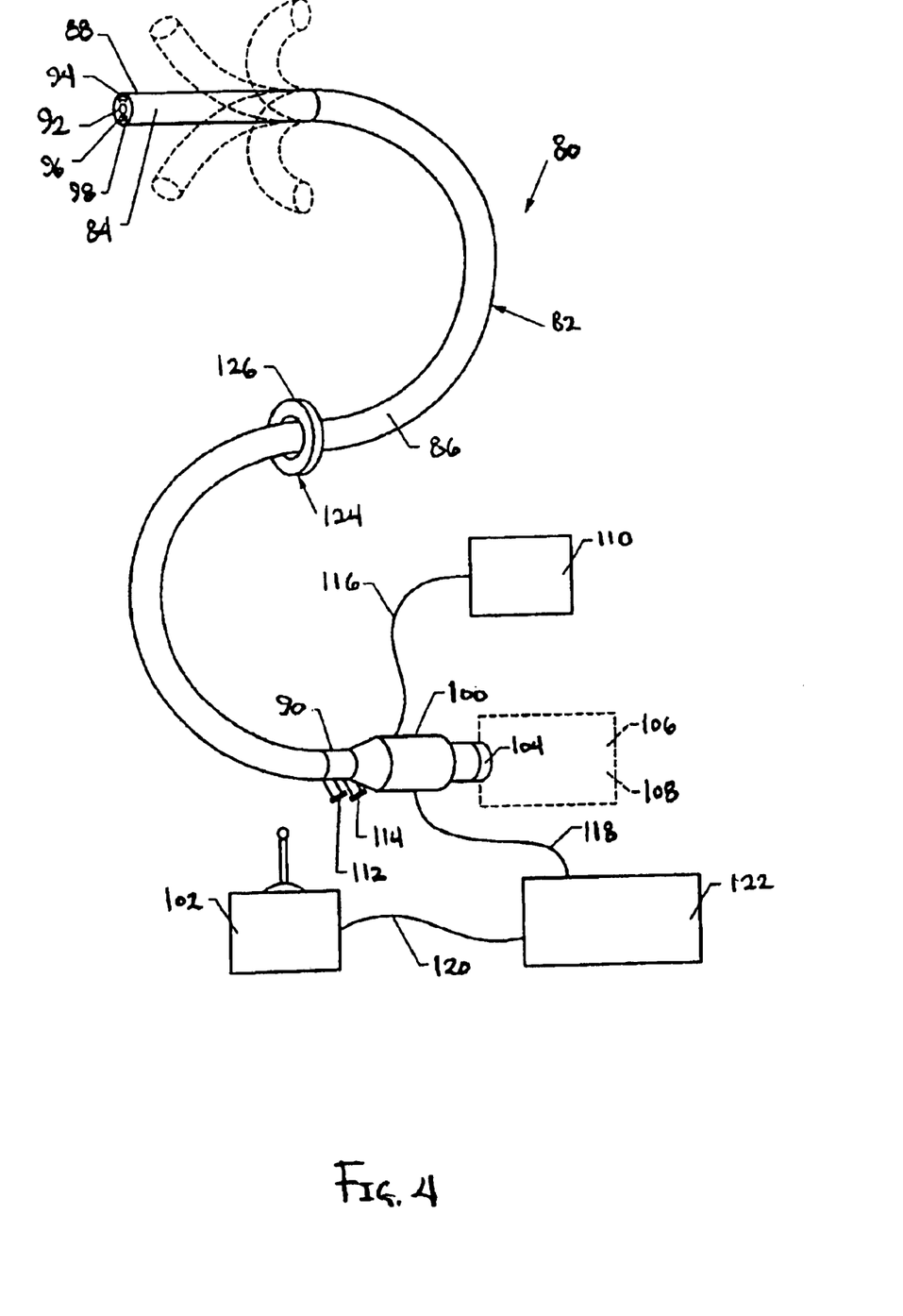
FIG. 4 shows a variation on a steerable endoscope having a selectively steerable distal portion and an automatically controllable proximal portion which may be used with the rigidizable guide tube.

One example of such an endoscope is shown in FIG. 4, which shows one variation of steerable endoscope 80. Endoscope 80 has an elongate body 82 with a manually or selectively steerable distal portion 84 and an automatically controlled proximal portion 86. The selectively steerable distal portion 84 can be selectively steered or bent up to a full 180° bend in any direction. A fiberoptic imaging bundle 92 and one or more illumination fibers 94 may extend through body 82 from proximal end 90 to distal end 88. Alternatively, endoscope 80 may be configured as a video endoscope with a miniaturized video camera, e.g., a CCD camera, positioned at distal end 88 of endoscope body 82. The images from the video camera may be transmitted to a video monitor by a transmission cable or by wireless transmission where images may be viewed in real-time or recorded by a recording device onto analog recording medium, e.g., magnetic tape, or digital recording medium, e.g., compact disc, digital tape, etc. Optionally, body 82 of endoscope 80 may include one or two instrument channels 96, 98 that may also be used for insufflation or irrigation, air and water channels, vacuum channels, etc. Body 82 of endoscope 80 is preferably highly flexible so that it is able to bend around small diameter curves without buckling or kinking while maintaining the various channels intact. When configured for use as a colonoscope, body 82 of the endoscope 80 may range typically from 135 to 185 cm in length and approximately 12–13 mm in diameter. Endoscope 80 can be made in a variety of other sizes and configurations for other medical and industrial applications.

A proximal handle 100 is attached to proximal end 90 of elongate body 82. Handle 100 may include ocular 104 connected to fiberoptic imaging bundle 92 for direct viewing and/or for connection to a video camera 106 or a recording device 108. Handle 100 may be connected to an illumination source 110 by illumination cable 116 that is connected to or continuous with illumination fibers 94. A first luer lock fitting 112 and a second luer lock fitting 114 on the handle 100 may be connected to instrument channels 96, 98.

Handle 100 may be connected to an electronic motion controller 122 by way of controller cable 118. Steering control 102 may be connected to electronic motion controller 122 by way of a second cable 120. Steering control 102 may allow the user to selectively steer or bend selectively steerable distal portion 84 of body 82 in the desired direction. Steering control 102 may be a joystick controller as shown, or other known steering control mechanism. Electronic motion controller 122 may control the motion of automatically controlled proximal portion 86 of body 82. The electronic motion controller 122 may be implemented using a motion control program running on a microcomputer or using an application-specific motion controller. Alternatively, electronic motion controller 122 may be implemented using, a neural network controller.

An axial motion transducer 124 may be provided to measure the axial motion of the endoscope body 82 as it is advanced and withdrawn. The axial motion transducer 124 can be made in many possible configurations. By way of example, the axial motion transducer 124 in FIG. 4 is configured as a ring 126 that may entirely or partially surround body 82 of endoscope 80. The axial motion transducer 124 is preferably attached to a fixed point of reference, such as the surgical table or the insertion point for endoscope 80 on the patient's body. As body 82 of endoscope 80 slides through axial motion transducer 124, it produces a signal indicative of the axial position of endoscope body 82 with respect to the fixed point of reference and sends a signal to electronic motion controller 122 by telemetry or by a cable (not shown). Axial motion transducer 124 may use optical, electronic or mechanical methods to measure the axial position of endoscope body 82. Other possible configurations for the axial motion transducer 124 are further described in copending U.S. patent application Ser. No. 09/969,927.

Figure 5:
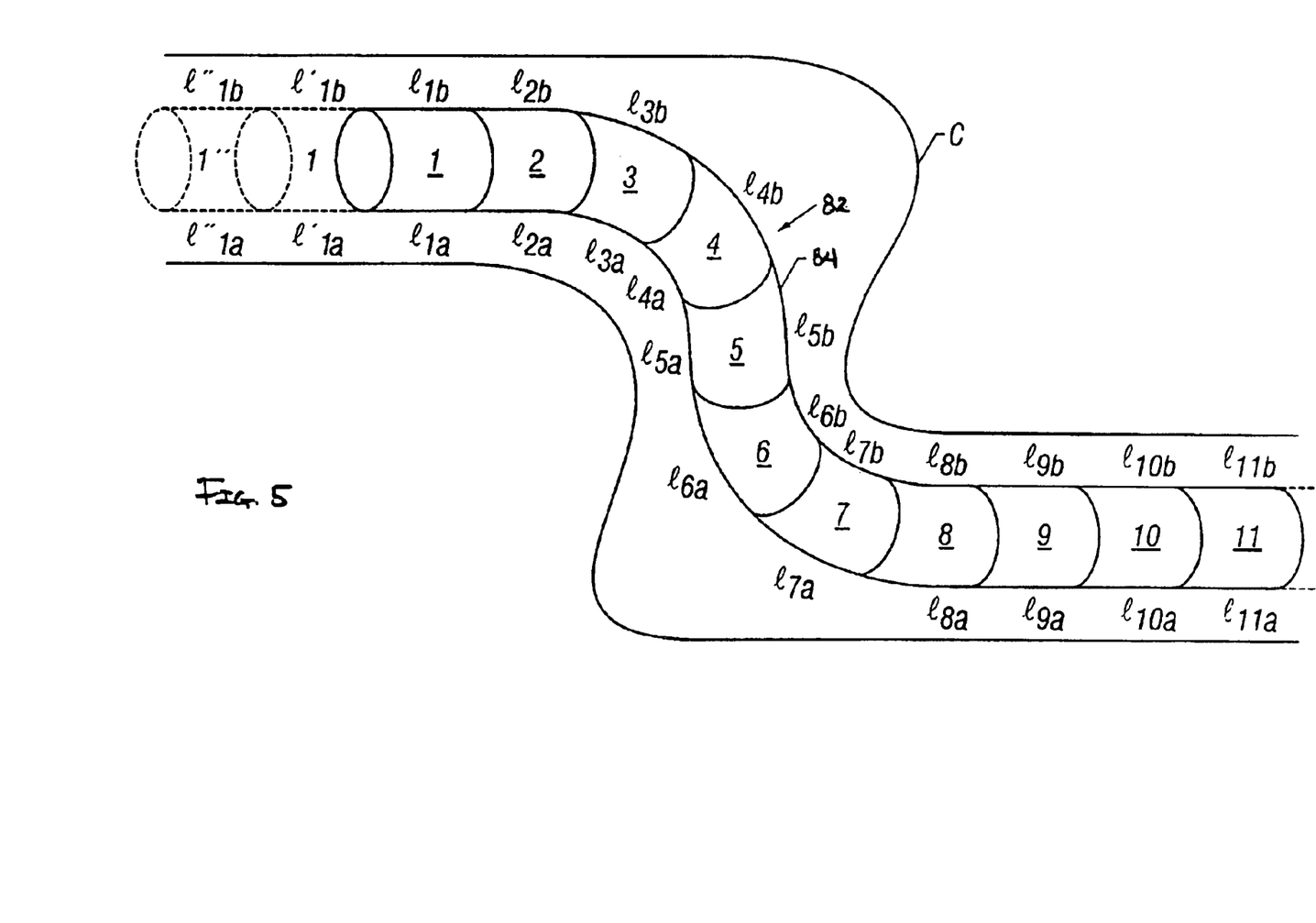
FIG. 5 shows a wire frame model of a section of the automatically controllable endoscope traversing an arbitrary curve.

FIG. 5 shows a wire frame model of a section of body 82 of endoscope 80 in a neutral or straight position. Most of the internal structure of endoscope body 82 has been eliminated in this drawing for the sake of clarity. Endoscope body 82 is divided up into segments or sections 1, 2, 3, . . . , etc. The geometry of each segment is defined by four length measurements along the a, b, c and d axes and each of the adjacent segments are preferably interconnected via joints which allow the independent angular movement and/or rotation of each segment relative to one another. For example, the geometry of segment 1 is defined by the four length measurements $1_{1a}$, $1_{1b}$, $1_{1c}$, $1_{1d}$, and the geometry of segment 2 is defined by the four length measurements $1_{2a}$, $1_{2b}$, $1_{2c}$, $1_{2d}$, etc. Each adjacent segment 1, 2, 3, . . . , etc., are preferably individually controlled by linear actuators (not shown), e.g., electric, pneumatic, hydraulic, etc. motors. The linear actuators may utilize one of several different operating principles. For example, to bend the endoscope body 82 in the direction of the a axis, the measurements $1_{1a}$, $1_{2a}$, $1_{3a}$ . . . $1_{10a}$ can be shortened and the measurements $1_{1b}$, $1_{2b}$, $1_{3b}$ . . . $1_{10b}$ would be lengthened an equal amount. The amount by which these measurements are changed determines the radius of the resultant curve. Alternatively, individual motors may be actuated to move adjacent segments relative to one another to effect a resultant curvature, as described in further detail in U.S. patent application Ser. No. 09/969,927.

In the automatically controlled proximal portion 86, each segment may be automatically controlled by electronic motion controller 122, which uses a curve propagation method to control the shape of endoscope body 82. Endoscope body 82 has been maneuvered through the curve in colon C with the benefit of selectively steerable distal portion 84 and now automatically controlled proximal portion 86 resides in the curve. When endoscope body 82 is advanced distally by one unit, segment 1 moves into the position marked 1', segment 2 moves into the position previously occupied by segment 1, segment 3 moves into the position previously occupied by segment 2, etc. The axial motion transducer 124 produces a signal indicative of the axial position of endoscope body 82 with respect to a fixed point of reference and sends the signal to the electronic motion controller 122, under control of the electronic motion controller 122, each time endoscope body 82 advances one unit, each segment in automatically controlled proximal portion 86 is signaled to assume the shape of the segment that previously occupied the space that it is now in. Thus, the curve propagates proximally along the length of automatically controlled proximal portion 86 of endoscope body 82. The curve appears to be fixed in space, as endoscope body 82 advances distally.

Similarly, when the endoscope body 82 is withdrawn proximally, each time endoscope body 82 is moved proximally by one unit, each segment in automatically controlled proximal portion 86 is signaled to assume the shape of the segment that previously occupied the space that it is now in. The curve propagates distally along the length of the automatically controlled proximal portion 86 of endoscope body 82, and the curve appears to be fixed in space, as endoscope body 82 withdraws proximally. Whenever endoscope body 82 is advanced or withdrawn, axial motion transducer 124 preferably detects the change in position and electronic motion controller 122 propagates the selected curves proximally or distally along automatically controlled proximal portion 86 of endoscope body 82 to maintain the curves in a spatially fixed position. This allows endoscope body 82 to move through tortuous curves without putting unnecessary force on the walls of colon C.

One example of using assembly 10, e.g., in the colon, the physician or surgeon may typically first advance distal portion 22 of endoscope 12 within the body of the patient. Upon reaching the first point at which endoscope 12 requires steering to negotiate a curved pathway, the user may appropriately steer distal portion 22 to assume a curve for traversing the pathway. At this point with endoscope 12 held stationary relative to the patient, guide tube 14 may be advanced over shaft 20 until the distal end of guide tube 14 is at, a short distance before, or a short distance past, the distal tip of controllable distal portion 22. The short distance is considered to range anywhere from a few centimeters to several inches. While guide tube 14 is advanced over shaft 20, tube 14 is preferably in a non-rigid state and is flexible enough to assume the curve formed by controllable distal portion 22.

Once tube 14, or at least its distal portion, has assumed the curve formed by controllable distal portion 22, tube 14 is rigidized preferably along its length to hold its assumed shape. Once this is accomplished, shaft 20 of endoscope 12 may be further advanced within the rigidized guide tube 14 to traverse the curved pathway without having to place any pressure against the walls of the colon.

Alternatively, if automatically controllable endoscope 80 is utilized, it may generally be used in the same manner as conventional endoscope 12. However, because endoscope body 82 is automatically controllable either along its entire length or along several segments proximally of steerable distal portion 84, the steerable distal portion 84 may be advanced farther past the distal end of guide tube 14 than might be possible with conventional endoscope 12. Controllable endoscope 80 may be used in all other aspects similarly as conventional endoscope 12 as described herein.

Returning to FIG. 1, bellows or covering 26 may cover distal opening 24 of guide tube 14 to prevent the entry of debris and fluids within guide lumen 16. As distal portion 22 of shaft 20 is advanced distally through tube 14 and out of guide lumen 16, covering 26 is preferably configured to expand distally either over or with shaft 20 while maintaining a seal with guide lumen 16. When shaft 20 is retracted within guide lumen 16 or when guide tube 14 is advanced distally relative to shaft 20, covering 26 is preferably configured to retract proximally back over distal opening 24 along with the proximal movement of distal portion 22. The use of covering 26 is optional and may be used to maintain the sterility of guide lumen 16. Covering 26 may also be used to prevent the pinching and tearing of tissue when shaft 20 is withdrawn within guide lumen 16.

Figure 2:
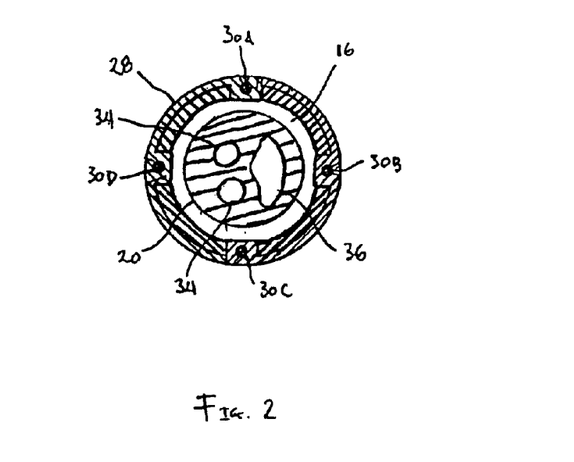
FIG. 2 shows a cross-sectional view of the guide tube assembly of FIG. 1.

Guide tube 14 may be any conventional appropriately flexible conduit which is capable of being rigidized along its entire length. The variation shown in FIG. 1 is comprised of a plurality of individual segments 28 which are linked adjacent to one another via several, i.e., more than one, tensioning wires or elements 30. Segments 28 may be a series of interconnecting ball-and-socket type segments which allow adjacent segments 28 to angularly pivot relative to one another to form an angle for traversing curves. These segments 28 may be rigidized via tensioning elements 30 which may be placed circumferentially about segments 28, as shown in FIG. 2, which is a cross-sectioned view of assembly 10 from FIG. 1. In this variation, there are four tensioning wires 30A, 30B, 30C, 30D which are each placed 90° relative to one another. Although four wires are shown in this example, a fewer number of wires may also be used, e.g., three wires. Each of these wires 30A, 30B, 30C, 30D may be routed through an integral channel or lumen defined in the walls of each segment 28. Moreover, they may be individually manipulated or they may all be manipulated simultaneously to effect a tensioning force for either rigidizing or relaxing guide tube 14 along its length.

FIG. 2 also shows the relative positioning of shaft 20 in relation to segment 28. As seen, shaft 20, which may contain any number of channels 34 for illumination fibers, optical fibers, etc., and working channels 34, is slidingly disposed within guide lumen 16. This variation shows a gap separation between the outer surface of shaft 20 and the inner surface of segment 28. This gap may vary depending upon the diameter of the endoscope being used and the desired cross-sectional area of guide tube 14, but a nominal separation is preferable to allow the uninhibited traversal of shaft 20 within guide lumen 16. An example of a rigidizable conduit structure which may be utilized as part of the present invention is shown and described in further detail in U.S. Pat. No. 5,251,611 to Zehel et al., which is incorporated herein by reference in its entirety.

The outer surface of guide tube 14 preferably has a tubular covering 32 which covers at least a majority of tube 14. Tubular covering 32 may provide a barrier between the debris and fluids of the body environment and the interior guide lumen 16, if also used with covering 26. Moreover, covering 26 may be an integral extension of tubular covering 32 and may accordingly be made from a continuous layer of material. Tubular covering 32 may also provide a lubricous cover to facilitate the insertion and movement of guide tube 14 along the walls of the body lumen as well as to provide a smooth surface inbetween the individual segments 28 to prevent the tissue from being pinched or trapped. Tubular covering 32 may be made from a variety of polymeric materials, e.g., PTFE, FEP, Tecoflex, etc.

Figure 3:
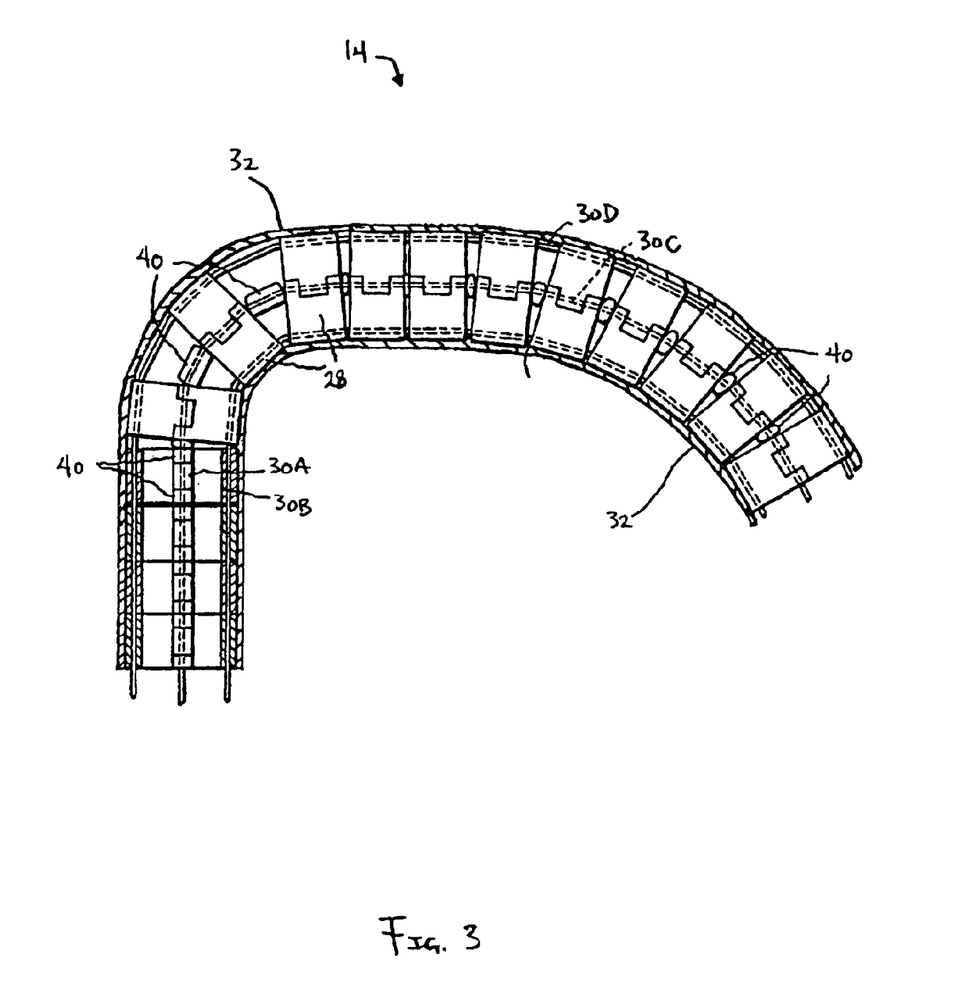
FIG. 3 shows the guide tube variation of FIG. 1 with a portion of the tube partially removed for clarity.

FIG. 3 shows a side view of guide tube variation 14 with a portion of the wall partially removed for clarity. As shown, individual segments 28 are aligned adjacent to one another with interconnecting sleeves 40 placed inbetween. Sleeves 40, in this variation, may be used to provide a pivoting structure to allow guide tube 14 to flex into different positions. Alternatively, segments 28 may be curved ball-and-socket type joints configured to interfit with one another. Tubular covering 32 may also be seen to cover at least the majority of guide tube 14. Optionally, a distal end portion of guide tube 14 may be configured to be controllable such that guide tube 14, like the controllable distal portion 22 of the endoscope 12, may define an optimal path for traversal.

Figure 6A:
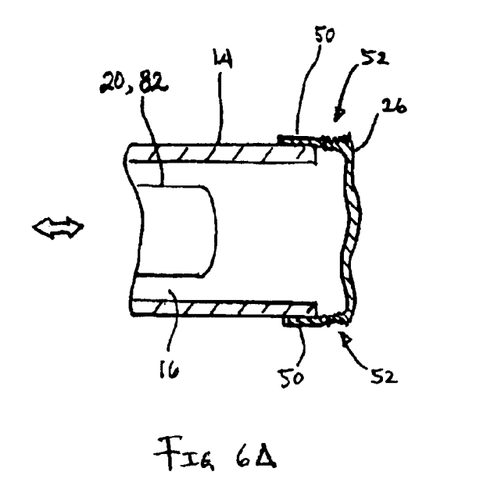
FIG. 6A shows a variation in which the distal end of the endoscope remains unattached to the flexible covering.

Bellows or covering 26 may optionally be appended to the distal end of conventional endoscope shaft 20 or controllable shaft 82. Throughout the description herein, automatically controllable endoscope 82 may be interchanged with conventional endoscope 12 when used in guide tube 14 as well as with the use of bellows or covering 26. Although descriptions on the method of use may describe use with conventional endoscope 12, this is done for brevity and is not intended to be limiting. The description is intended to apply equally to use with controllable endoscope 80 since the two may be easily interchanged depending upon the desired use and result. FIG. 6A shows one variation in which shaft 20 or 80 is unattached to covering 26 such that endoscope 12 may be freely inserted and withdrawn from guide lumen 16. Covering 26 may be omitted altogether from the assembly but is preferably used not only to help maintain an unobstructed guide lumen 16, but also to prevent the walls of the body lumen from being pinched between the endoscope shaft 20 or 80 and guide tube 14 during advancement of the assembly. As seen in FIG. 6A, covering 26 may be separately attached at attachment region 50 to the outer surface or distal edge of guide tube 14. Covering 26 may also further comprise a gusseted region 52 which allows the covering 26 to be compressed into a small compact profile and expanded much like a bellows during shaft 20 or 80 advancement. When shaft 20 or 80 is withdrawn, gusseted region 52 may allow covering 26 to recompress or reconfigure itself back into its compacted shape. In this variation, covering 26 is unattached to shaft 20 or 80; therefore, once the assembly has reached a predetermined location within the colon, covering 26 may be removed through a working channel within endoscope 12 or the working tools may simply be pierced through covering 26, although this is less preferable, before a procedure may be begin.

Figure 6B:
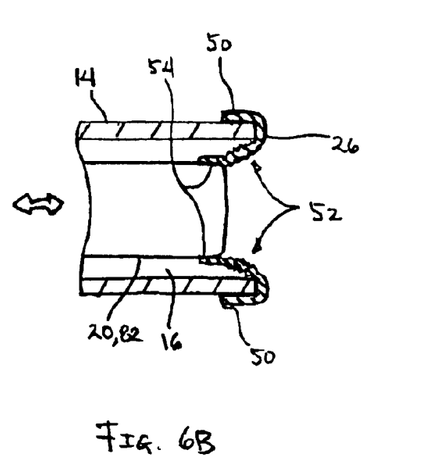
FIG. 6B shows another variation in which the distal end of the endoscope is attached to the flexible covering.
Figure 7:
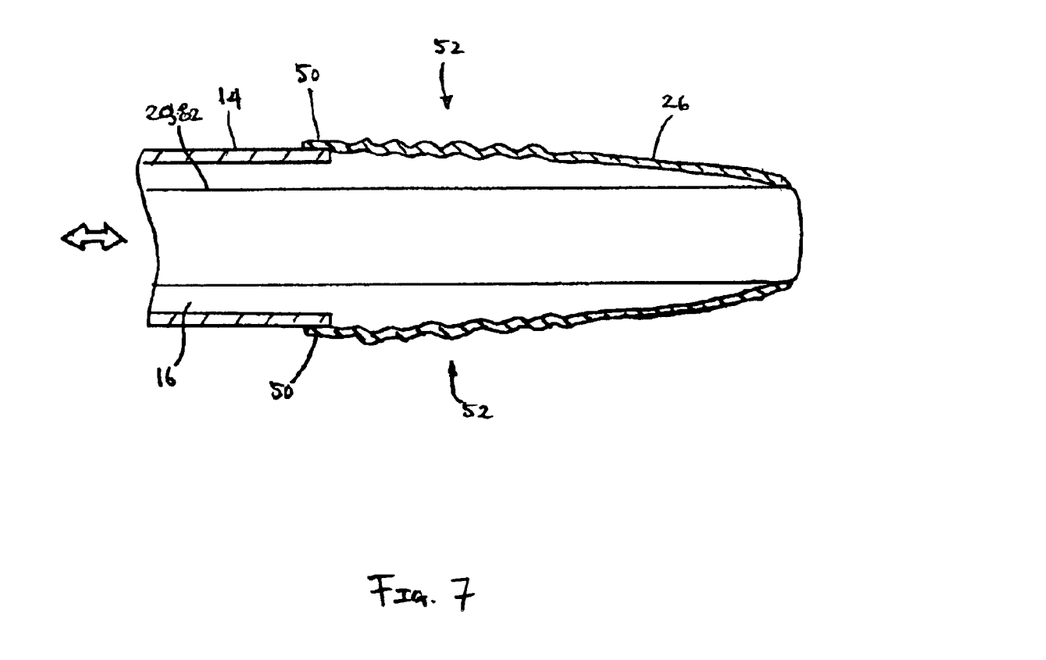
FIG. 7 shows the distal end of the endoscope extending past the distal end of the guide tube and the flexible covering extending distally along with the endoscope.

FIG. 6B shows another variation where covering 26 may be attached to the endoscope shaft 20 or 80 near or at the distal end of controllable distal portion 22 along attachment region 54. As shaft 20 or 80 is advanced or withdrawn from guide lumen 16, covering 26 remains attached to the endoscope 12. FIG. 7 shows shaft 20 or 80 being advanced to a distal position through guide lumen 16. As shaft 20 or 80 is advanced, gusseted region 52 may be seen expanding to accommodate the distal movement. The gusseted region 52 may be configured to allow shaft 20 or 80 to be advanced to any practical distance beyond guide tube 14, e.g., a few or several inches, depending upon the application. With this variation, shaft 20 or 80 may be extended through guide lumen 16 to this distal position prior to first advancing shaft 20 or 80 within the colon of a patient as well as to allow enough room so that the controllable distal portion 22 may have enough space to be manipulated to assume a desired shape or curve over which guide tube 14 may be advanced over.

Figure 8A:
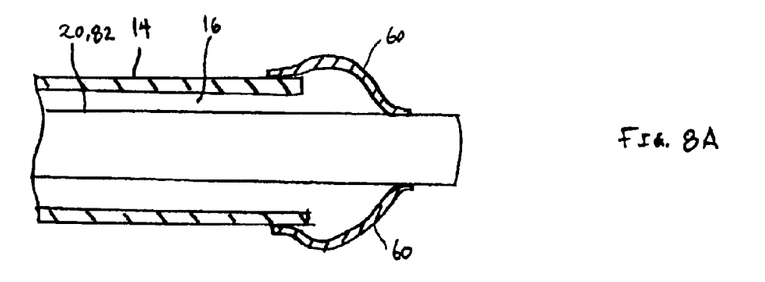
FIG. 8A shows another variation in which the covering is configured as an elastic tubular structure.
Figure 9:
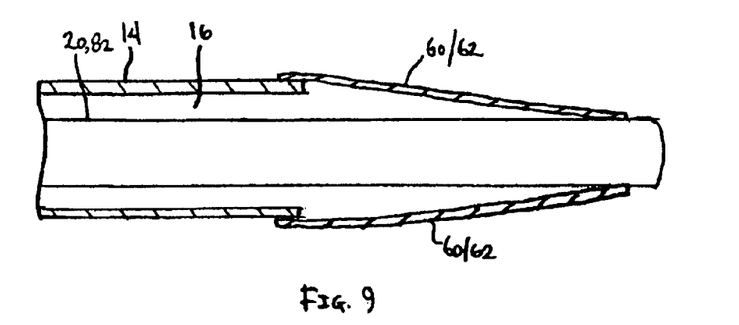
FIG. 9 shows the variations of FIGS. 8A and 8B in which the endoscope is extended distally.

Another variation is shown in FIG. 8A in which covering 60 may be configured as an elastic tubular member. As seen, when endoscope shaft 20 or 80 is in a retracted position, covering 60 may be configured to form a tubular structure when relaxed. As endoscope shaft 20 or 80 is advanced distally, as seen in FIG. 9, covering 60 may stretch along with shaft 20 or 80 to maintain the sterility of guide lumen 16.

Figure 8B:
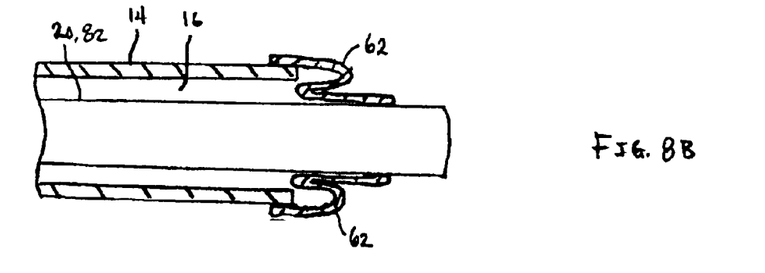
FIG. 8B shows another variation in which the covering is configured as an elastic diaphragm structure.

Yet another variation is shown in FIG. 8B in which covering 62 may be configured as an elastic rolling diaphragm. When endoscope shaft 20 or 80 is retracted, covering 62 may be configured to evert upon itself such that part of covering 62 may be pulled proximally into guide lumen 16. Such a covering 62 material may comprise any number of elastomers, elastomeric materials, or rubber-type materials, e.g., neoprene or latex. When endoscope shaft 20 or 80 is advanced distally, covering 62 may likewise revert and stretch distally along with shaft 20 or 80, also as shown in FIG. 9.

Figure 10:
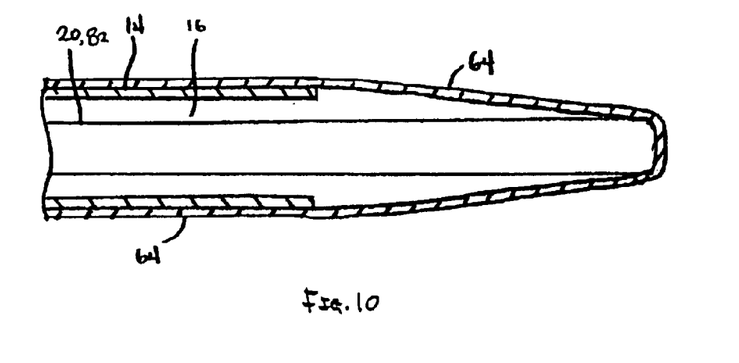
FIG. 10 shows yet another variation in which a plastic covering is used to cover the endoscope and guide tube.

Alternatively, the covering may simply be a plastic covering or wrapper 64 which is non-elastic, as shown in FIG. 10. Such coverings 64 are conventionally available and may be advanced along with endoscope shaft 20 or 80 and retracted likewise as endoscope shaft 20 or 80 is retracted.

Figure 11A:
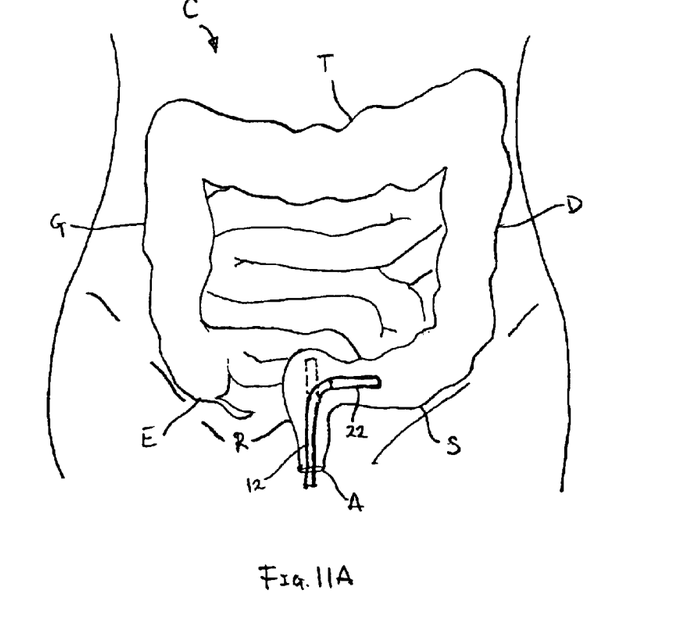
FIGS. 11A to 11E show a variation on advancing an endoscope through a colon using the guide tube as support.

FIGS. 11A to 11E show one variation of advancing a conventional endoscope 12 using the guide tube 14. FIG. 11A shows an illustrative colon C of a patient. Endoscope 12 may be inserted within colon C through the anus A of the patient. As the distal portion 22 is advanced through rectum R, it encounters its first point of curvature. Here, controllable distal portion 22 may be manipulated much as a conventional endoscope to select an optimal path into sigmoid colon S. The optimal path is one which presents the most efficient path for advancing endoscope 12 with the least amount of contact against the walls of colon C.

Figure 11B:
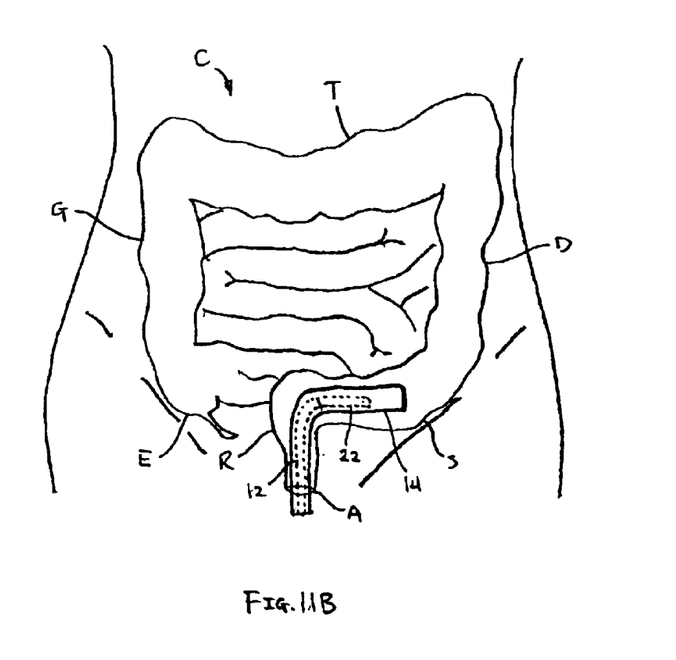

Once distal portion 22 has been manipulated to select the appropriate shape, guide tube 14 may be advanced through anus A and rectum R over endoscope 12 while endoscope 12 is maintained stationary relative to colon C. Guide tube 14 is preferably in a relaxed state and is able to conform easily to the shape defined by controllable distal portion 22. Guide tube 14 may be advanced to the distal end of distal portion 22, a short distance before, or a short distance past the distal end of portion 22, as shown in FIG. 11B. Once guide tube 14 has been advanced distally, it may be rigidized along its length such that it maintains the shape defined by endoscope 12.

Figure 11C:
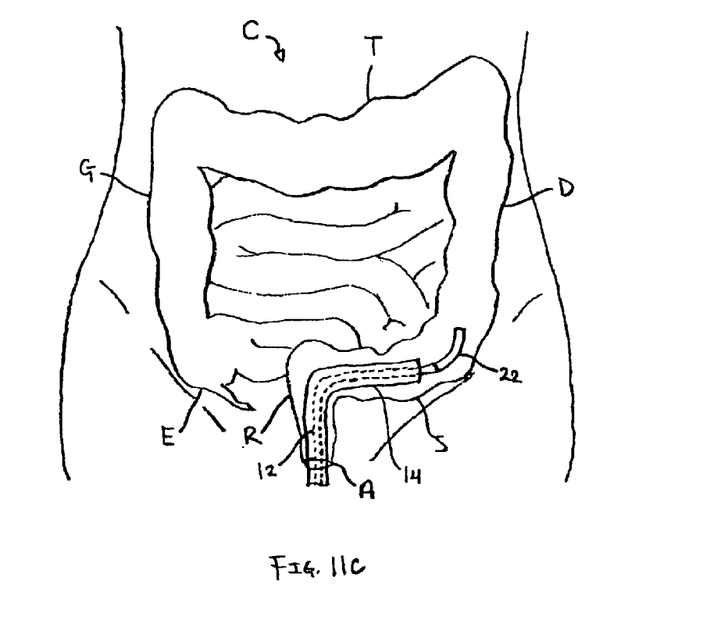
Figure 11D:
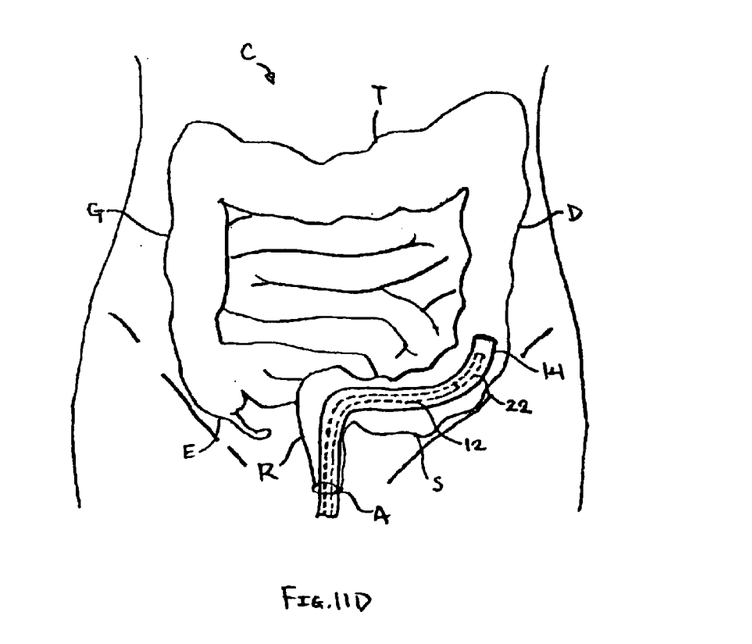
Figure 11E:
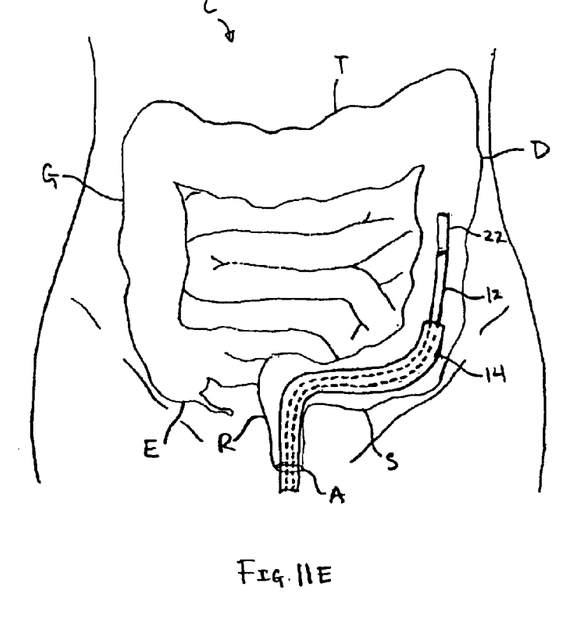

Then, with guide tube 14 rigidized, it is preferably held stationary relative to colon C while endoscope 12 is further advanced through guide tube 14 until distal portion 22 reaches the next point of curvature. Controllable distal portion 22 may then be manipulated to select an optimal path into descending colon D, as shown in FIG. 11C. Once the optimal path has been selected, endoscope 12 is preferably maintained stationary relative to colon C while guide tube 14 is placed into its relaxed state and advanced over endoscope 12. Guide tube 14 may be advanced distally until the distal end of endoscope 12 is reached, as shown in FIG. 11D. At this point, guide tube 14, having assumed the shape defined by controllable distal portion 22, may be rigidized along its length to maintain this shape. Endoscope 12 may then be advanced distally again, as seen in FIG. 11E, while using the rigidized guide tube 14 to provide the column strength to advance endoscope 12 without the need to unnecessarily contact the walls of colon C. Endoscope 12 may be advanced until distal portion 22 reaches the flexure between descending colon D and transverse colon T. Once this point is reached, the steps described above may be repeated as necessary until endoscope 12 has negotiated its way through transverse colon T, and ascending colon G until cecum E has been reached, or until a desired location within colon C has been reached.

Figure 12:
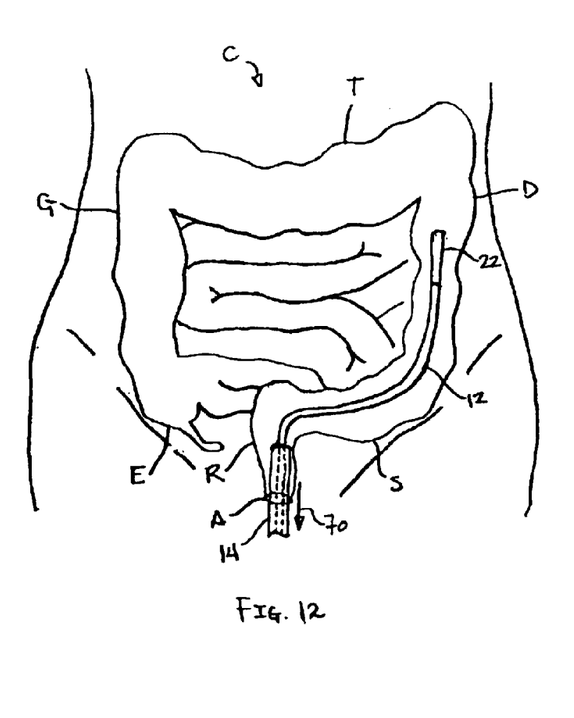
FIG. 12 shows a variation in which the guide tube may be withdrawn from the colon while leaving the endoscope behind.

At any point during the exploratory procedure, guide tube 14 may be removed from colon C while leaving endoscope 12 behind, as shown in FIG. 12 by tube withdrawal 70. If endoscope 12 were left within colon C, the endoscope 12 may be used and manipulated as any conventional endoscope or colonoscope would be during a conventional colonoscopy examination. Guide tube 14 may also be partially retracted to allow the distal portion 22 to be steered or manipulated to examine or treat the colon C while still providing support and guidance to the proximal scope section of endoscope 12. To remove the assembly from colon C, guide tube 14 may first be withdrawn, as shown, and endoscope 12 may be subsequently withdrawn. Alternatively, the above steps may be repeated in reverse order to withdraw both guide tube 14 and endoscope 12 from colon C.

The applications of the guide tube system and methods of use discussed above are not limited to regions of the body but may include any number of further treatment applications. Other treatment sites may include areas or regions of the body around organ bodies. Additionally, the present invention may be used in other environments which present tortuous paths such as exploratory procedures on piping systems, ducts, etc. Moreover, various other rigidizable guide tube apparatus and applications may be utilized beyond what is described herein. Modification of the above-described assemblies and methods for carrying out the invention, and variations of aspects of the invention that are obvious to those of skill in the art are intended to be within the scope of the claims.

What is claimed is:

1. A system for advancing an endoscope through a tortuous path, comprising:

an endoscope shaft having a proximal end, a controllable distal end, and a length therebetween; and an elongate guide tube having a length which defines a lumen therethrough and wherein the guide tube is adapted to slidingly receive the endoscope shaft within the lumen, the guide tube further comprising at least one tensioning member disposed along the length of the guide tube for selectively rigidizing the length of the guide tube, wherein at least a portion of the guide tube is further adapted to conform to and maintain a shape defined by the controllable distal end when the tensioning member is under a tensioning force.

2. The system of claim 1 wherein the endoscope shaft comprises a conventional endoscope shaft.

3. The system of claim 1 wherein the endoscope shaft comprises an elongate body having a proximal end and a selectively steerable distal end and defining at least one lumen therebetween, the elongate body comprising a plurality of segments interconnected via joints, and at least one motor attached to each of at least a majority of segments for actuating an adjacent segment and wherein each motor is independently controllable, wherein when the distal end assumes a selected curve, the plurality of segments are configured to propagate the selected curve along the elongate body by each motor selectively actuating the adjacent segment.

4. The system of claim 1 wherein the guide tube comprises a plurality of segments which are connected adjacently, wherein at least a majority of the segments are angularly movable relative to one another.

5. The system of claim 1 wherein the guide tube comprises at least three tensioning members disposed along the length of the guide tube.

6. The system of claim 5 wherein each of the tensioning members are located circumferentially relative to one another about the guide tube.

7. The system of claim 1 further comprising a tubular covering disposed over at least a majority of an outer surface of the guide tube.

8. The system of claim 1 further comprising a covering disposed over a distal end of the guide tube lumen.

9. The system of claim 8 wherein the covering comprises a gusseted region which is adapted to expand from a first compressed configuration to a second longitudinally expanded configuration as the endoscope shaft is advanced distally relative to the distal end of the guide tube lumen.

10. The system of claim 8 wherein the covering is adapted to evert upon itself when the endoscope shaft is positioned within the guide tube lumen.

11. The system of claim 8 wherein the covering is adapted to stretch distally when the endoscope shaft is advanced distally relative to the distal end of guide tube.

12. The system of claim 8 wherein the covering is attached between the distal end of the guide tube and along a distal location on the endoscope shaft.

13. The system of claim 8 wherein the covering is attached between the distal end of the guide tube and over the distal end of the endoscope shaft.

14. The system of claim 8 wherein the covering is disposed entirely over the distal end of the guide tube lumen and the distal end of the endoscope shaft.

15. A method of advancing an endoscope along a path, comprising:

advancing an endoscope shaft along the path until a curve in the path is encountered;

manipulating a controllable distal end of the endoscope shaft to assume a shape to traverse the curve;

advancing a guide tube in a flexible state over the endoscope shaft such that a portion of the guide tube assumes the shape defined by the controllable distal end of the endoscope shaft;

applying tension to rigidize a length of the guide tube such that the shape is maintained by the guide tube; and further advancing the endoscope shaft through the rigidized guide tube.

16. The method of claim 15 further comprising relaxing the guide tube.

17. The method of claim 15 further comprising preventing tearing of surrounding tissue during relative movement between the guide tube and the endoscope shaft.

18. The method of claim 15 further comprising preventing pinching of surrounding tissue during relative movement between the guide tube and the endoscope shaft.

19. The method of claim 15 wherein the guide tube is advanced over the endoscope shaft until a distal end of the guide tube is located adjacent with, just proximally, or just distally of the distal end of the endoscope shaft.

20. The method of claim 15 wherein manipulating the controllable distal end of the endoscope comprises manually controlling the distal end to assume the shape.

21. The method of claim 15 further comprising expanding a covering disposed over the distal end of the guide tube as the endoscope shaft is advanced distally relative to the guide tube.

22. The method of claim 15 wherein applying tension to rigidize a length of the guide tube comprises tensioning at least one tensioning member disposed along the length of the guide tube.

23. The method of claim 15 wherein applying tension to rigidize a length of the guide tube comprises compressing guide tube segments.

24. The method of claim 15 wherein the guide tube shape is maintained by compressing adjacent guide tube segments.

25. A method of advancing an endoscope through a path, comprising:

advancing an endoscope shaft along the path until a curve in the path is encountered;

manipulating a controllable distal end of the endoscope shaft to assume a shape to traverse the curve;

advancing a segmented guide tube in a flexible state over the endoscope shaft such that a portion of the guide tube assumes the shape defined by the distal end of the endoscope shaft; and maintaining the assumed shape of the guide tube by compressing at least two guide tube segments.

26. The method of claim 25 further comprising preventing tearing of surrounding tissue during relative movement between the guide tube and the endoscope.

27. The method of claim 25 further comprising preventing pinching of surrounding tissue during relative movement between the guide tube and the endoscope.

28. The method of claim 25 further comprising expanding a cover configured to expand distally either over or with the endoscope shaft.

* * * * *